United States Patent
Golarits et al.

(10) Patent No.: US 10,525,189 B2
(45) Date of Patent: Jan. 7, 2020

(54) EXTRACORPOREAL ALARM SUPPRESSION METHOD AND DEVICE

(71) Applicant: B. BRAUN AVITUM AG, Melsungen (DE)

(72) Inventors: István Golarits, Budapest (HU); Botond Tényi, Budakalász (HU); Ferenc Tegzes, Göd (HU)

(73) Assignee: B. Braun Avitum AG (DE)

( * ) Notice: Subject to any disclaimer, the term of this patent is extended or adjusted under 35 U.S.C. 154(b) by 378 days.

(21) Appl. No.: 15/474,098

(22) Filed: Mar. 30, 2017

(65) Prior Publication Data
US 2017/0296736 A1 Oct. 19, 2017

(30) Foreign Application Priority Data
Apr. 15, 2016 (EP) ..................................... 16165552

(51) Int. Cl.
*A61M 1/36* (2006.01)
*A61M 1/26* (2006.01)
*G06F 19/00* (2018.01)

(52) U.S. Cl.
CPC .......... *A61M 1/3656* (2014.02); *A61M 1/267* (2014.02); *G06F 19/3418* (2013.01);
(Continued)

(58) Field of Classification Search
CPC ................ A61M 1/267; A61M 1/3656; A61M 2205/18; A61M 2205/3331;
(Continued)

(56) References Cited

U.S. PATENT DOCUMENTS

| 8,298,167 B2 | 10/2012 | Peters et al. |
| 2015/0306301 A1 | 10/2015 | Strohhoefer et al. |
| 2016/0095971 A1 | 4/2016 | Kopperschmidt et al. |

FOREIGN PATENT DOCUMENTS

| DE | 10 2013 008720 | 11/2014 |
| EP | 1 110 566 | 6/2001 |

(Continued)

OTHER PUBLICATIONS

European Search Report for EP 16 16 5552 dated Sep. 20, 2016.

*Primary Examiner* — Benjamin J Klein
(74) *Attorney, Agent, or Firm* — RatnerPrestia

(57) ABSTRACT

An extracorporeal alarm suppression method is arranged to be carried out in a continuous renal replacement therapy and/or chronic hemodialysis device and includes the steps of monitoring vascular access pressure, including arterial and/or venous pressure, of a patient using a vascular access pressure monitoring means; detecting an access pressure alarm situation if the arterial or venous pressure is out of predetermined alarm limits; when a first access pressure alarm situation is detected, setting the device to an alarm suppression state reducing the blood flow and therapy flows using an alarm suppression state setting means; detecting that a predetermined alarm suppression state condition is met using a predetermined alarm suppression state condition detecting means, the predetermined alarm suppression state condition including at least a predetermined waiting time having passed or a parameter threshold having been reached after the first access pressure alarm situation has been detected; and when a further access pressure alarm situation is detected after the predetermined alarm suppression state condition has been met, setting the device to a safety state using a safety state setting means, the safety state being a state in which the blood pump is stopped.

12 Claims, 1 Drawing Sheet

(52) U.S. Cl.
CPC . *A61M 2205/18* (2013.01); *A61M 2205/3331* (2013.01); *A61M 2205/3334* (2013.01); *A61M 2205/3344* (2013.01); *A61M 2205/3351* (2013.01); *A61M 2205/3355* (2013.01); *A61M 2205/505* (2013.01)

(58) Field of Classification Search
CPC .. A61M 2205/3334; A61M 2205/3344; A61M 2205/3351; A61M 2205/3355
See application file for complete search history.

(56) References Cited

FOREIGN PATENT DOCUMENTS

| | | |
|---|---|---|
| EP | 2 913 071 | 9/2015 |
| WO | WO 03/082144 | 10/2003 |
| WO | WO 2009/144522 | 12/2009 |

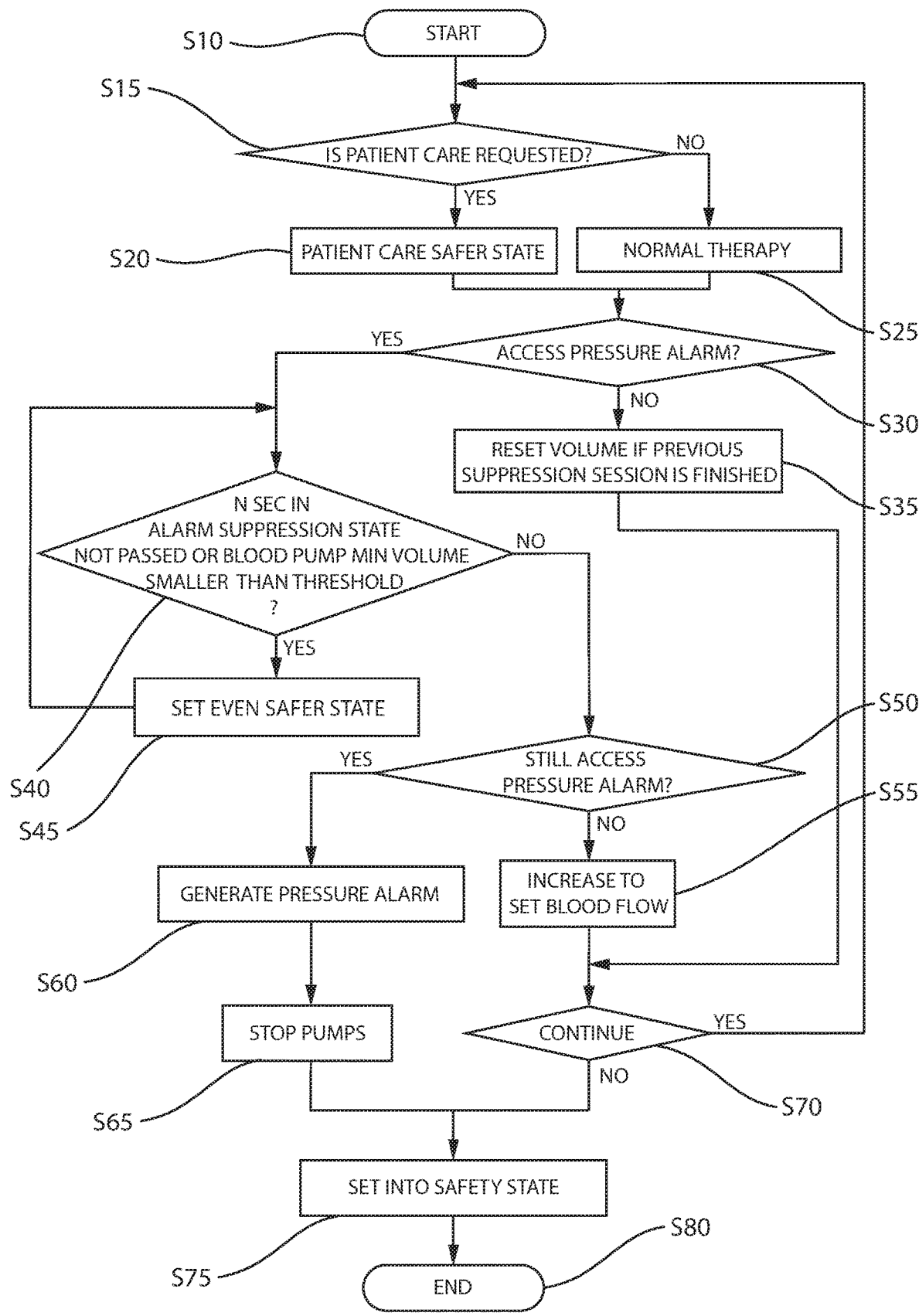

EXTRACORPOREAL ALARM SUPPRESSION METHOD AND DEVICE

CROSS REFERENCE TO RELATED APPLICATIONS

This application claims priority to European application EP 16165552.7 filed Apr. 15, 2016, the contents of such application being incorporated by reference herein.

FIELD OF THE INVENTION

The invention relates to apparatuses and methods for continuous and intermittent renal therapies and/or extracorporeal blood treatment, such as dialysis therapies and/or plasma therapies, and in particular to extracorporeal alarm suppression in such methods and apparatuses.

BACKGROUND OF THE INVENTION

Known hemodialysis systems are designed to carry out blood therapy procedures such as slow continuous ultrafiltration (SCUF), continuous veno-venous hemofiltration (CVVH), continuous veno-venous hemodialysis (CVVHD) or continuous veno-venous hemodiafiltration (CVVHDF). These continuous renal replacement therapies are referred to as CRRT and designed for removal of metabolic waste and excess fluid from patients in fluid overload and who need renal support. As such, CRRT is a dialysis modality used to treat critically ill, hospitalized patients in the intensive care unit who develop acute kidney injury (AKI). Unlike chronic kidney disease, which occurs slowly over time, AKI often occurs in hospitalized patients treated in an intensive care environment, and it typically occurs over a few hours to a few days. Plus chronic haemodialysis system as well (HD, HDF, . . . ).

DESCRIPTION OF THE RELATED ART

As one of known devices in the a.m. CRRT field, U.S. Pat. No. 8,298,167 B2 describes an apparatus comprising a control unit with blood and fluid pumps, a manually installed replaceable panel kit mounted on the control unit having blood and fluid supply tubing on the panels, a replaceable filter cartridge, a controller CPU configured for operating the system including blood pump and fluid pumps and an interactive operator control system with an operator interface screen operatively connected to the controller. The controller CPU comprises one or more microprocessors provided with software configured to operate the apparatus in response to operator input selections and provide apparatus operating instructions and status of selected therapy parameters. The interactive operator control system is characterized by operator inputs for selecting a CRRT patient therapy, changing the panel kit, replacing the filter cartridge and changing to a different patient therapy from a currently running patient therapy without changing the panels or the filter cartridge. The operator input control panel also provides step-by-step operator instructions for changing the panel kit, replacing a filter cartridge and changing patient therapy during a running patient therapy. The interactive user control system utilizes an operator interface touchscreen with graphic controls whereby the operator may select system operations and is provided with instructions for carrying out the selected system operations and patient therapy sessions. The system also provides operator selection of temporary patient disconnect and later start procedure during a current selected therapy session as well as detailed operator instructions for carrying out the procedures.

During CRRT, pressure alarms can occur as one of frequent types of alarms, especially on the blood circuit (arterial and venous sides). In this respect, it is known to automatically adapt the blood flow rate as compared to the blood pressure monitoring (low or high pressure in arterial or venous line) and to avoid incessant blood pump stops (coagulation problems) leading to additional nurse work and also lowering the renal dose, or to carry out an arterial pressure suppression process in a certain patient care or cleaning mode. However such suppression is not effective in case of frequent pressure pulses occurring successively one after another, and the process is not yet implemented for venous pressure.

During a blood purification therapy of the aforementioned kind pressure alarms may be generated due to e.g. a movement of a patient, a short-term kinking of the blood line, or in case of a patient cleaning procedure rendering temporary arterial and/or venous pressure changes, or pulses. Issuing alarms in such cases is disturbing for an operator. Accordingly, there is a need for an additional alarm suppression caused by temporary arterial and venous pressure pulses even with reduced blood flow.

SUMMARY OF THE INVENTION

Therefore, an object of the present invention resides in providing an apparatus and/or a method for CRRT, the apparatus and/or method being capable of taking into account temporary arterial and venous pressure pulses or changes caused during CRRT and improving on the frequency of alarm issuance under such temporary arterial and venous pressure pulses or changes.

According to aspects of the present invention, this object is achieved by an extracorporeal alarm suppression method and device as defined in the independent claims. Advantageous further developments of the invention are subject of the accompanying dependent claims.

Focusing on false alarms caused by short negative arterial or positive venous pressure pulses due to e.g. patient movement or short-term kinking of the blood line, or during cleaning the patient in a blood purification therapy, while keeping the extracorporeal blood running, a general idea underlying the present invention resides in providing a control process reducing the number of extracorporeal pressure alarms while ensuring the proper safety of the patient by temporarily setting a system into a safer state and to thereby reduce the probability that pressure spikes reach the alarm limits during the same time period. A special patient care mode is selectable within a given safety volume limit, or automatically for a given period, which period can be arranged to be repeated for pressure pulses occurring frequently one after another within a safety volume limit. This allows pressure spikes to decay during this time period so that a false alarm is suppressed. Advantages of the present invention reside in a more effective suppression of frequent subsequent pressure pulses and a process for venous pressure as well.

More specifically, according to an aspect of the present invention, an extracorporeal alarm suppression method arranged to be carried out in a continuous renal replacement therapy device includes the steps of monitoring vascular access pressure, including arterial and/or venous pressure, of a patient using a vascular access pressure monitoring means (controller); detecting an access pressure alarm situation if the arterial or venous pressure is out of predetermined alarm limits; when a first access pressure alarm situation is detected, setting the device to an alarm suppression state by reducing the blood flow and therapy flows using an alarm suppression state setting means (controller); detecting that a predetermined alarm suppression state condition is met using a predetermined alarm suppression state condition detecting means (controller), the predetermined alarm suppression state condition including at least a predetermined waiting time having passed or a parameter threshold having been reached after the first access pressure alarm situation has been detected; and when a further access pressure alarm situation is generated detected after the predetermined alarm suppression state condition has been met, setting the device to a safety state using a safety state setting means (controller), the safety state being a state in which the blood pump is stopped.

Preferably, the vascular access pressure is monitored in either of at least a first and a second predetermined operational mode of the device, the first predetermined operational mode being a patient care mode and the second predetermined operational mode being a normal mode.

Also preferably, there may be a step of determining whether or not the first predetermined device operational mode has been selected, wherein the patient care mode includes operating the device with patient care mode parameters that are changed toward values being safer for a patient compared to normal mode parameters applied in a normal mode of the device, wherein if it is determined that the first predetermined device operational mode has been selected, operating the device using said patient care mode parameters, and if it is determined that the first predetermined device operational mode has not been selected, operating the device using said normal state parameters.

Also preferably, said first predetermined device operational mode is a patient care mode, and the patient care mode parameters include a reduced blood pump flow, an at least temporary halt of the therapy, and/or a widening of pre-filter and/or venous pressure limits while arterial pressure limits are kept unchanged.

Also preferably, an alarm informing an operator is generated after a predetermined period of time in said patient care mode has lapsed, and the predetermined period of time in said patient care mode is resettable for repetition until the patient care mode is deselected by the operator.

Also preferably, the alarm suppression state is a first safer state of the device and includes operating the device with parameters that are changed toward safer values compared to parameters applied in a normal state of the device.

Also preferably, when it is determined that the arterial or venous pressure exceeds either of a predetermined arterial lower or venous upper alarm limit, an automatic pressure alarm suppression mode is carried out in which the safety state of the device is set automatically and independently of whether the first or second predetermined operational mode is operative.

Also preferably, in the automatic pressure alarm suppression mode the blood pump flow is reduced from an original flow value to a minimum flow value for a given period of time, the therapy is at least temporarily halted and pre-filter and venous pressure limits are widened while the arterial pressure limits are kept unchanged.

Also preferably, said pre-filter and venous pressure limits are widened to the same values as those in the first predetermined operational mode.

Also preferably, when it is determined during said automatic pressure alarm suppression mode that the arterial or venous pressure no longer exceeds either of a predetermined arterial lower or venous upper alarm limit, the blood pump flow is increased from the minimum flow value to the original flow value during a blood flow increasing period.

Also preferably, the automatic pressure alarm suppression mode is repeated if it is determined that any of the alarm limits are reached again.

Also preferably, said automatic pressure alarm suppression mode is disabled automatically after a predetermined overall mode active period of time has lapsed, and an alarm is generated.

According to another aspect of the invention, an extracorporeal alarm suppression device in a continuous renal replacement therapy device is provided, wherein the extracorporeal alarm suppression device is configured to carry out the method according one of the preceding claims.

As used herein, the method and apparatus described and referred to herein may be configured to not only carry out a variety of different renal replacement therapies and continuous fluid management for continuous renal replacement therapy (CRRT) but also for separating plasma from blood, treating plasma to remove toxins and excess fluid and for therapeutic apheresis and chronic haemodialysis. An interactive operator control feature can include an operator interface that provides apparatus operating instructions and therapy status and parameters. The interface may be a touch-screen interface. However, other well-known interfaces, such as those that use conventional buttons or switches are also contemplated. As used herein, an input device can be, for example, a keyboard, rollerball, mouse, voice recognition system or other device capable of transmitting information from a user to a computer. The input device can also be a touch screen associated with the display, in which case the user responds to prompts on the display by touching the screen. The user may enter textual information through the input device such as the keyboard or the touch-screen. As used herein, instructions refer to computer-implemented steps for processing information in the system. Instructions can be implemented in software, firmware or hardware and include any type of programmed step undertaken by components of the system. A Local Area Network (LAN) or Wide Area Network (WAN) may be a corporate computing network, including access to the Internet, to which computers and computing devices comprising the system are connected. The LAN may conform to the Transmission Control Protocol/Internet Protocol (TCP/IP) industry standard.

BRIEF DESCRIPTION OF THE DRAWINGS

The invention is best understood when read in connection with the accompanying drawing.

FIG. 1, provided schematically and simplified, shows steps in a false and/or extracorporeal, respectively, alarm suppression process or method carried out in an apparatus configured to be used in a CRRT environment and the like.

DETAILED DESCRIPTION OF PREFERRED EMBODIMENTS

Generally speaking, depending on a pending situation, the reduction of the number of extracorporeal pressure alarms can be achieved by selecting a special mode by the operator within a given safety volume limit in case of patient cleaning/mobilization with further automatic alarm suppression, or automatically for a given period in case of e.g. patient movement or short-term kinking of the blood line, which period can be repeated for pressure pulses frequently after each other within a safety volume limit.

The false alarm suppression process or method, or extracorporeal alarm suppression control, as provided in the form of an extracorporeal alarm suppression method or an extracorporeal alarm suppression device configured to carry out the said method, is visualized in the FIGURE including at least the following steps. It is noted that as mentioned above a general CRRT apparatus suitable for CRRT and the like as such is well known in the art and details thereof will not be explained redundantly.

According to the drawing, starting with a step S10, the method and/or device according to present embodiment in particular include the following steps and/or configurations.

In a step S15, it is determined whether or not an operator has selected a patient care or cleaning mode (IsPatientCareRequested). If the determination in step S15 is affirmative (step S15: YES), the process proceeds to a step S20 wherein a patient care or safer state is set as a first predetermined operational mode in which the blood pump flow is reduced (Patient Care State; BloodPump=Run_WithReducedBloodFlow), the therapy is stopped (Therapy=Stop), and/or pre-filter and venous pressure limits are widened (VPPressurelimits=OpenForSuppression), while the arterial pressure limits are kept unchanged. An alarm may inform the operator about a too long patient care mode after a given time, which alarm and/or time is configured to be resettable. In accordance with this embodiment, this mode can be continued until it is e.g. deselected by the operator. If the determination in step S15 is negative (step S15: NO), the process proceeds to a step S25 in which, as a second predetermined operational mode, the blood pump and the therapy are kept running with already, or originally, set flows (Normal Therapy Run; BloodPump=Run_WithSetBloodFlow, Therapy=Run). After each of steps S20 and S25, the process continues to a step S30.

In step S30, it is determined whether or not there is an access pressure alarm situation (whether or not an access pressure alarm situation is occurring). An access pressure alarm is determined to occur either when a detected access pressure is lower than an arterial pressure lower limit (AP<APLowLimit) or higher than a venous pressure upper limit (VP>VPHighLimit). If the determination in step S30 is affirmative (step S30: YES), the process proceeds to a step S40.

In this respect, "access pressure alarm" means that the arterial pressure is lower than the predefined alarm limit and/or the venous pressure is higher than the predefined alarm limit.

In step S40, indicating the case in which the arterial or venous pressure is out of predetermined alarm limits (either the arterial lower or the venous upper limit), independently of whether the system is in patient care mode (the first predetermined operational mode) or in normal operation (the second predetermined operational mode), it is determined whether the process has to remain in an even safer state or to leave the even safer state.

In the even safer state, the process or system is set to a state in a step S45 which is even safer than the patient care state (or patient care mode) in which the blood pump is operated with already reduced blood flow, by setting an alarm suppression state or an automatic pressure alarm suppression mode with very low blood flow and/or in which the blood pump flow is reduced to a minimum flow (BloodPump=Run_WithBPMin), the therapy flow is reduced and/or the therapy is stopped (Therapy=Stop), and/or pre-filter and venous pressure limits are widened (VP/FP PressureLimits=OpenForSuppression, i.e. to the same limits as in case of the aforementioned patient care mode), while the arterial pressure limits are unchanged.

As shown in the FIGURE, the process proceeds from step S40 to step S45 unconditionally once the occurrence of an access pressure alarm has been determined in step S30.

The determination in step S40 as to whether the process has to remain in the even safer state or to leave the even safer state means a determination corresponding to "wait for N seconds in the alarm suppression state or stop waiting if BPMinVolume>xml (where BPMinVolume+=d(BloodPumpVolume)". In other words, it is determined in step S40 whether a given period of time (TimeOfBPMin) to avoid the stop of the blood pump against coagulation and false alarms has passed or not (TimeOfBPMin<N seconds) or whether the blood pump minimum volume (BPMinVolume) is smaller than a predetermined volume (xml) or not: ((TimeOfBPMin<N sec) or (BPMinVolume<xml)). In other words, as long as the said given period of time (TimeOfBPMin) has not passed or as long as the blood pump minimum volume (BPMinVolume) is smaller than the predetermined volume, the process loops through steps S40 and S45 (step S40: YES). If the said given period of time (TimeOfBPMin) has passed or if the blood pump minimum volume (BPMinVolume) is equal to or larger than the predetermined volume (step S40: NO), the process proceeds to a step S50.

It is noted that the process automatically sets the even safer state in step S45 in order to reduce pressure spikes, and that in case of an immediate negative determination in step S40 (step S40: NO) the process proceeds to a step S50.

In step S50, it is again determined whether or not there is still an access pressure alarm situation (whether or not an access pressure alarm situation is still occurring). An access pressure alarm situation is determined to occur either when a detected access pressure is lower than an arterial pressure lower limit (AP<APLowLimit) or higher than a venous pressure upper limit (VP>VPHighLimit). If the determination in step S50 is affirmative (step S50: YES), the process proceeds to a step S60.

In step S60, a pressure alarm is generated in order to inform the operator. The generated pressure alarm may be configured to indicate low arterial pressure (APLow) or high venous pressure (VPHigh): PressureAlarm=APLow or VPHigh. Then, the process proceeds to a step S65 in which the process stops pumps due to the generated pressure alarm, e.g. by using sort of a break instruction. In the subsequent step S75, the machine or device is set or placed into a safety state in which the blood pump is stopped (BloodPump=Stop), the therapy is stopped (Therapy=Stop), and the blood pump minimum volume is set to zero (BPMinVolume=0). Thereafter, the process ends in a step S80.

Otherwise, if the determination in step S50 is negative (step S50: NO), the process proceeds to a step S55. In step S55, if pressures are not in the alarm range any more while the automatic pressure alarm suppression mode is activated, the blood pump flow is increased back to the original, or earlier, set blood flow (set normal flow or Run_WithReducedBloodFlow).

If any of the alarm limits is reached again during the aforementioned blood flow increasing period, the process returns to step S15 and then S30 and the automatic pressure alarm suppression mode is repeated. This is basically achieved using a step S70.

In step S70, it is determined whether or not a process execution condition is met or not. In the present embodiment, the process execution condition is configured to always return the process flow to step S15 until an automatic pressure alarm suppression mode activation time limit is reached.

Once returned to step S15 from step S70, the process is configured to either repeat the automatic pressure alarm suppression mode as described above, or to quickly loop, in the absence of an access pressure alarm in step S30 (step S30: NO), through a step S35 in which the blood pump minimum volume is reset if the respective previous suppression session is finished, and step S70. In this case, without patient care being requested in step S15 and without an access pressure alarm being generated in step S30, the automatic pressure alarm suppression mode is stopped and the blood pump and the therapy is running with original flows.

Regarding the aforementioned process execution condition, the process and the device may be configured so that an overall period of time in the automatic pressure alarm suppression mode, i.e. an overall activation time of the automatic pressure alarm suppression mode, is limited in order to keep a delivered blood volume within an uncritical range (BPMinVolume) as a protective measure against accidental blood loss to the environment. Upon reaching this activation time limit the process and the device may be further configured to disable the automatic pressure alarm suppression mode and to generate a corresponding alarm (PressureAlarm).

In the present embodiment, for example, if it is determined in step S70 that the automatic pressure alarm suppression mode activation time limit has been reached (indicating that access pressure alarm situations are too frequently or constantly generated in each process execution run) (step S70: NO), the process proceeds as well to step S75 wherein the machine or device is set or placed into a safety state in which the blood pump is stopped (BloodPump=Stop), the therapy is stopped (Therapy=Stop), and the blood pump minimum volume is set to zero (BPMinVolume=0). Thereafter, the process ends in step S80.

The invention disclosed herein may be implemented as a method, apparatus or article of manufacture using standard programming or engineering techniques to produce software, firmware, hardware, or any combination thereof. The term "article of manufacture" as used herein refers to code or logic implemented in hardware or computer readable media such as optical storage devices, and volatile or non-volatile memory devices. Such hardware may include, but is not limited to, field programmable gate arrays (FPGAs), application specific integrated circuits (ASICs), complex programmable logic devices (CPLDs), programmable logic arrays (PLAs), microprocessors, or other similar processing devices.

Although specific instructions of an overall system and control environment, such as for example steps prior to step S10 and steps following step S80, are not shown, such operation is within the purview of the system described hereinabove as will be understood to those skilled in the art. It is also to be understood that the specific text, sequence and content of process shown in the drawing and described herein are by way of illustration and example only and the apparatus, systems and operations thereof are not to be limited thereby.

Therefore and as understood, the invention is not limited to the described preferred embodiment and modifications thereof, and combinations of at least parts of the embodiment, modifications and equivalents all within the scope defined by the appended claims may occur to the skilled person.

The invention claimed is:

1. An extracorporeal alarm suppression method arranged to be carried out in at least one of a continuous renal replacement therapy or a chronic haemodialysis device, the method including the steps of:
   monitoring vascular access pressure, including at least one of arterial or venous pressure, of a patient;
   detecting an access pressure alarm situation if the arterial or venous pressure is out of predetermined alarm limits;
   when a first access pressure alarm situation is detected, setting a hemodialysis device to an alarm suppression state by reducing the blood flow and therapy flows, the hemodialysis device including a blood pump;
   detecting that a predetermined alarm suppression state condition is met, the predetermined alarm suppression state condition including at least one of a predetermined waiting time having passed or a blood pump minimum volume having exceeded a predetermined volume after the first access pressure alarm situation has been detected; and
   when a further access pressure alarm situation is detected after the predetermined alarm suppression state condition has been met, setting the hemodialysis device to a safety state wherein the blood pump is stopped;
   wherein the vascular access pressure is monitored in either of at least a first and a second predetermined operational mode of the hemodialysis device, as determined by an operator selection, the first predetermined operational mode is a patient care mode and the second predetermined operational mode is a normal mode, wherein the patient care mode includes operating the hemodialysis device with patient care mode parameters that are changed toward values being safer for the patient compared to normal mode parameters applied in the normal mode of the hemodialysis device and the patient care mode parameters include at least one of a reduced blood pump flow, an at least temporary halt of the therapy, a widening of pre-filter pressure limits, or a widening of venous pressure limits while arterial pressure limits are kept unchanged.

2. The method according to claim 1, including a step of:
   determining if the first predetermined device operational mode has been selected, wherein if it is determined that the first predetermined device operational mode has been selected, operating the device using said patient care mode parameters; and
   if it is determined that the first predetermined device operational mode has not been selected, operating the device using said normal state parameters.

3. The method according to claim 1, wherein said first predetermined device operational mode is a patient care mode.

4. The method according to claim 3, wherein
   an alarm informing an operator is generated after a predetermined period of time in said patient care mode has lapsed; and
   the predetermined period of time in said patient care mode is resettable for repetition until the patient care mode is deselected by the operator.

5. The method according to claim 1, wherein
   the alarm suppression state is a first safer state of the hemodialysis device and includes operating the hemodialysis device with parameters that are changed toward safer values compared to parameters applied in a normal state of the hemodialysis device.

6. The method according to claim 1, wherein
when it is determined that the arterial or venous pressure exceeds either of a predetermined arterial lower or venous upper alarm limit, an automatic pressure alarm suppression mode is carried out in which the safety state of the hemodialysis device is set automatically and independently of whether the first or second predetermined operational mode is operative.

7. The method according to claim 6, wherein in the automatic pressure alarm suppression mode:
a blood pump flow is reduced from an original flow value to a minimum flow value for a given period of time;
the therapy is at least temporarily halted; and
pre-filter and venous pressure limits are widened while the arterial pressure limits are kept unchanged.

8. The method according to claim 7, wherein said pre-filter and venous pressure limits are widened to the same values as those in the first predetermined operational mode.

9. The method according to claim 7, wherein
when it is determined during said automatic pressure alarm suppression mode that the arterial or venous pressure no longer exceeds either of a predetermined arterial lower or venous upper alarm limit, the blood pump flow is increased from the minimum flow value to the original flow value during a blood flow increasing period.

10. The method according to claim 8, wherein the automatic pressure alarm suppression mode is repeated if it is determined that any of the alarm limits are reached again.

11. The method according to claim 6, wherein said automatic pressure alarm suppression mode is disabled automatically after a predetermined overall mode active period of time has lapsed, and an alarm is generated.

12. An extracorporeal alarm suppression system in a hemodialysis device including a blood pump, the hemodialysis device comprising:
a vascular access pressure monitor configured to monitor a vascular access pressure, including at least one of arterial or venous pressure, of a patient;
an access pressure alarm situation detector configured to detect an access pressure alarm situation if the arterial or venous pressure is out of predetermined alarm limits;
an alarm suppression state setting means configured to set the hemodialysis device to an alarm suppression state by reducing the blood flow and therapy flows, when a first access pressure alarm situation is detected;
a predetermined alarm suppression state condition detector configured to detect whether a predetermined alarm suppression state condition is met, the predetermined alarm suppression state condition including at least a predetermined waiting time having passed or a blood pump minimum volume having exceeded a predetermined volume after the first access pressure alarm has been generated; and
a safety state setting means configured to set the hemodialysis device to a safety state, when a further access pressure alarm situation is detected after the predetermined alarm suppression state condition has been met, the safety state being a state in which the blood pump is stopped;
wherein the extracorporeal alarm suppression system is configured to carry out the method according to claim 1.

* * * * *